United States Patent
Beyer et al.

(10) Patent No.: US 11,305,128 B1
(45) Date of Patent: Apr. 19, 2022

(54) DEFIBRILLATOR DISCHARGE TESTING

(71) Applicant: Avive Solutions, Inc., San Francisco, CA (US)

(72) Inventors: Rory M. Beyer, San Mateo, CA (US); Andreea F. Martin, San Francisco, CA (US)

(73) Assignee: Avive Solutions, Inc., San Francisco, CA (US)

( * ) Notice: Subject to any disclaimer, the term of this patent is extended or adjusted under 35 U.S.C. 154(b) by 102 days.

(21) Appl. No.: 16/923,385

(22) Filed: Jul. 8, 2020

Related U.S. Application Data

(60) Provisional application No. 62/871,915, filed on Jul. 9, 2019.

(51) Int. Cl.
*A61N 1/39* (2006.01)
*A61N 1/04* (2006.01)

(52) U.S. Cl.
CPC ........... *A61N 1/3904* (2017.08); *A61N 1/046* (2013.01); *A61N 1/3937* (2013.01)

(58) Field of Classification Search
CPC ..... A61N 1/3904; A61N 1/046; A61N 1/3937
See application file for complete search history.

(56) References Cited

U.S. PATENT DOCUMENTS

| | | | |
|---|---|---|---|
| 4,328,808 A | 5/1982 | Charbonnier et al. | |
| 5,824,017 A | 10/1998 | Sullivan et al. | |
| 5,827,326 A | 10/1998 | Kroll et al. | |
| 6,104,953 A | 8/2000 | Leyde | |
| 6,185,458 B1 * | 2/2001 | Ochs | A61N 1/3937 607/5 |
| 6,230,054 B1 * | 5/2001 | Powers | A61N 1/3937 607/5 |
| 6,421,563 B1 | 7/2002 | Sullivan et al. | |
| 6,477,413 B1 * | 11/2002 | Sullivan | A61N 1/3904 607/5 |
| 6,865,417 B2 | 3/2005 | Rissmann et al. | |
| 6,952,607 B2 | 10/2005 | Mulhauser | |
| 6,968,230 B2 | 11/2005 | Waltman | |
| 6,980,856 B2 | 12/2005 | Sullivan et al. | |
| 7,194,303 B2 | 3/2007 | Rissmann et al. | |
| 7,680,533 B2 | 3/2010 | Garrett et al. | |
| 8,301,245 B2 | 10/2012 | Garrett et al. | |
| 8,983,599 B2 | 3/2015 | Garrett et al. | |
| 9,387,337 B2 | 7/2016 | Garrett et al. | |
| 2004/0044371 A1 | 3/2004 | Tamura et al. | |
| 2004/0172068 A1 | 9/2004 | Sullivan et al. | |
| 2005/0021094 A1 | 1/2005 | Ostroff et al. | |

(Continued)

OTHER PUBLICATIONS

Medtronic, Physio-Control "Lifepak 12 defibrillator/monitor series Service Manual", 1998-2001, 849 pages.

*Primary Examiner* — Catherine M Voorhees
(74) *Attorney, Agent, or Firm* — Beyer Law Group LLP

(57) ABSTRACT

A variety of methods and discharge test circuits are described that are well suited for testing H-bridge based defibrillator discharge circuits. The H-bridge includes four switches and two outputs. In one aspect, a test discharge circuit is provided that includes a resistive element and a switch that are coupled to the second H-bridge output. The H-bridge and test circuit may be controlled to test various aspects of the H-bridge based defibrillator discharge circuit.

24 Claims, 4 Drawing Sheets

(56) References Cited

U.S. PATENT DOCUMENTS

| | | | |
|---|---|---|---|
| 2008/0077189 A1* | 3/2008 | Ostroff | A61N 1/3706 607/27 |
| 2016/0274162 A1* | 9/2016 | Freeman | A61N 1/39 |
| 2017/0252571 A1* | 9/2017 | Dascoli | A61N 1/3987 |

* cited by examiner

DEFIBRILLATOR DISCHARGE TESTING

CROSS REFERENCE TO RELATED APPLICATIONS

This application claims priority of U.S. Provisional Application No. 62/871,915, filed on Jul. 9, 2019, which is incorporated herein by reference in its entirety.

FIELD

The present disclosure relates generally to defibrillator discharge testing.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes in to cardiac arrest. By way of example, AEDs may be found in corporate and government offices, shopping centers, airports, airplanes, restaurants, casinos, hotels, sports stadiums, schools, fitness centers and a variety of other locations where people may congregate.

AEDs will often sit in place for extended periods of time (often years) without being used for their intended purpose. Yet it is important that the AED be fully operational in the relatively rare circumstances in which a particular AED needs to be used. Therefore, most AEDs periodically perform self-tests to verify that they remain operational. Although existing AEDs and existing self-test techniques work well, there are continuing efforts to develop improved self-testing capabilities.

SUMMARY

A variety of methods and discharge test circuits are described that are well suited for testing H-bridge based defibrillator discharge circuits. In general, an H-bridge includes first, second, third and fourth switches, an input electrically coupled to a shock delivery capacitor, a first output configured to be electrically coupled to a first defibrillation electrode pad and a second output configured to be electrically coupled to a second defibrillation electrode pad.

In one aspect a test discharge circuit is described that includes or consists essentially of a test resistive element and a fifth switch. The test resistive element is electrically coupled to the second output between the fifth switch and the second output such that current passing between the second output to the second defibrillation electrode does not pass through the test resistive element, and such that electrical current passing between the second output and the fifth switch does pass through the test resistive element.

The defibrillator controller is configured to direct operation of the switches of the H-bridge in an operational mode to deliver a defibrillation shock, and to direct operation of the switches of the H-bridge and the test discharge circuit in a test mode to facilitate testing at least portions of the H-bridge while at least partially discharging the shock delivery capacitor through the fifth switch.

In some embodiments, to facilitate testing the discharge circuit, the defibrillator controller directs the discharge capacitor to be charged to a suitable test voltage. The second and fifth switches are turned on with the first, third and fourth switches off for a first test phase. This causes the shock delivery capacitor to at least partially discharge through the second and fifth switches and the test resistive element. The charging of the shock discharge capacitor and the initiation of the first test phase tests the high voltage switching ability of the second switch and the dielectric strength of each of the first, second and fourth switches of the H-bridge.

In some embodiments, the capacitor voltage is monitored during the discharge and when the discharge capacitor reaches a designated threshold voltage, at least one of the second and fifth switches is turned off to halt the discharge. In some embodiments, the halting of the discharge in this manner provides a mechanism for verifying the defibrillator controller's ability to precisely control the discharge circuit based on the sensed voltage of the discharge capacitor.

In some embodiments, a second test phase is initiated by turning the first and third switches on with the second, fourth and fifth switches turned off with the shock discharge capacitor at the designated threshold voltage. The threshold voltage may be chosen such that a high current passes through the first and third switches during the second test phase—as for example peak test currents of 20 amps or more. This tests both the switching abilities of switches one and three and their ability to handle the large currents that are associated with delivering a defibrillation shock.

In some embodiments, another test involves charging the shock delivery capacitor with the second and fourth switches turned on and the first, third and fifth switches turned off. This tests the switching ability of the second and fourth switches which can be verified by monitoring the voltage of the discharge capacitor. When the second and fourth switches are working properly, the voltage on the capacitor will not rise since the capacitor is shorted to ground.

In some embodiments, a resistive element is positioned in an electrical path between the shock delivery capacitor and the first H-bridge output such that current passing from the shock delivery capacitor to the first H-bridge output passes through the resistive element but current passing from the shock delivery capacitor to the second H-bridge switch does not.

In some embodiments, the resistance of the resistive element associated with the first switch is in the range of 1 to 10 ohms. In some embodiments, the resistance of the test resistive element is in the range of 100 to 10,000 ohms.

In another aspect, turning the second and fifth switches on with the other H-bridge switches off causes the shock delivery capacitor to at least partially discharge through a discharge path consisting essentially of the second switch, the test resistive element and the fifth switch.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

The present invention relates generally to the testing of defibrillator discharge circuitry and defibrillator discharge testing circuitry.

Figure 1:
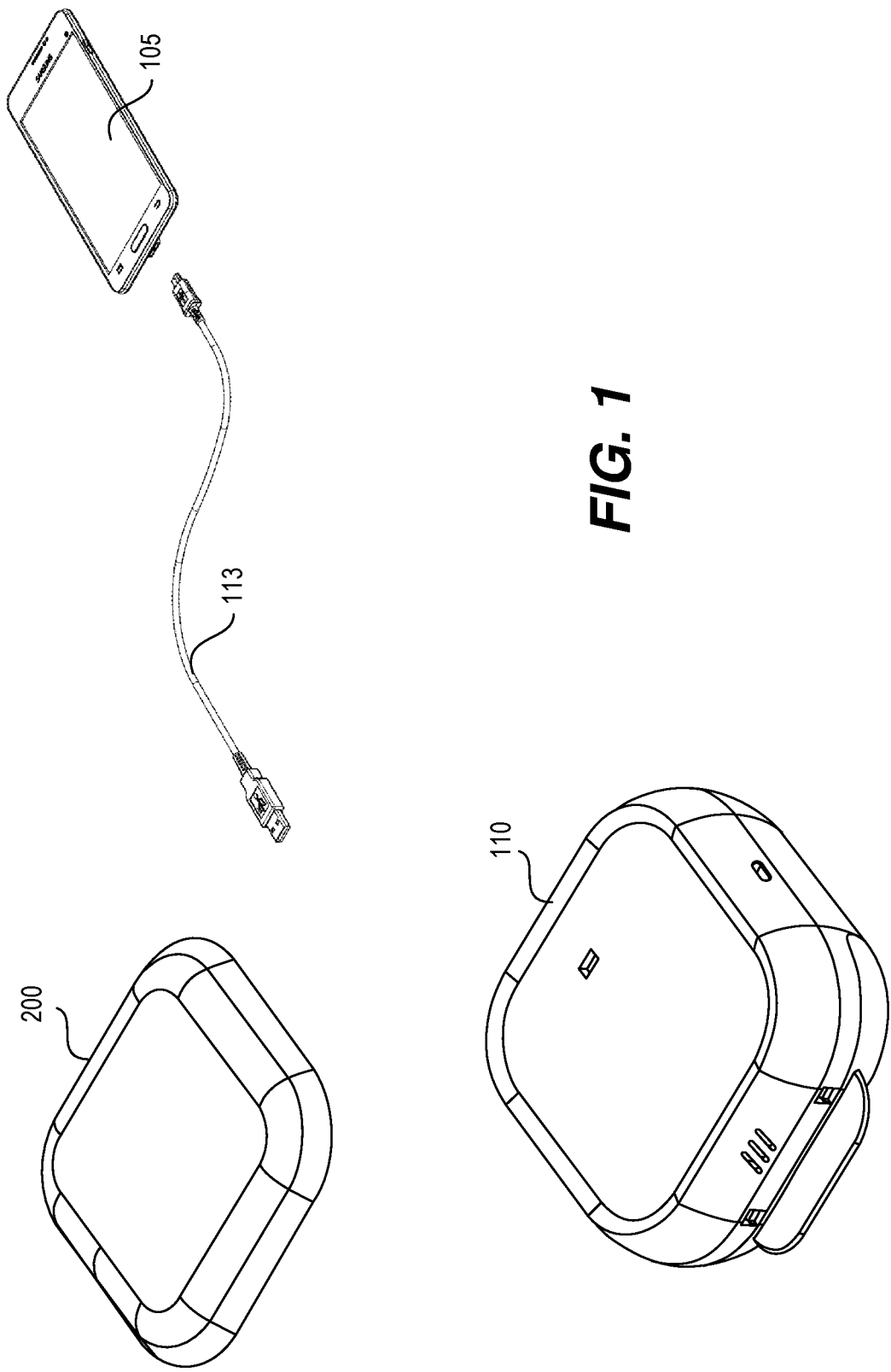
FIG. 1 is a block diagram of a modular defibrillator system architecture.

FIG. 1 illustrates a representative modular defibrillator system architecture. The illustrated architecture is well suited for use in automated external defibrillators (including both semi-automated and fully automated defibrillators) although it may also be used in manual defibrillators and hybrid defibrillators that may be used in either automated or manual modes. The core of the modular defibrillator system is a base defibrillation unit (base unit) 110. The base defibrillation unit 110 is a fully functional AED that is configured so that its functionality can be supplemented by attaching an interface unit 200 to the base unit 110 or by connecting the base unit 110 to a mobile communication device 105 (such as a smartphone, a tablet computer, etc.) having a defibrillator support app installed thereon (e.g., via connector 113). In some embodiments, a charging pack or other supplemental power storage unit can be attached to the base defibrillation unit to recharge a battery on the base unit, as appropriate, thereby effectively extending the base unit's usable life without an outside charge or battery replacement. U.S. patent application Ser. Nos. 16/145,657; 16/146,096 and 16/146,743 (each of which is incorporated herein by reference) describe a few such modular defibrillator systems.

Figure 2:
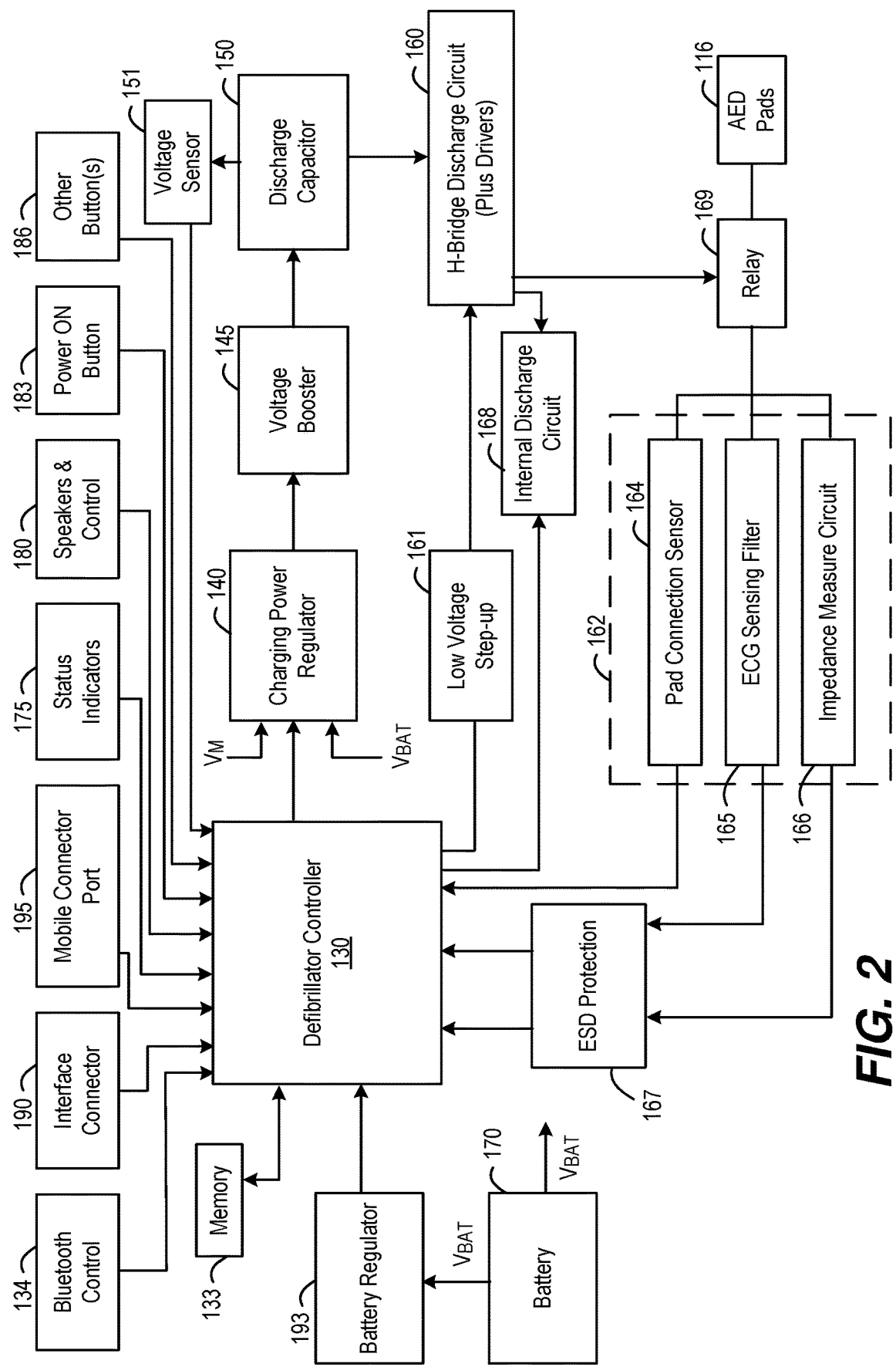
FIG. 2 is a block diagram illustrating electrical components of an embodiment of an AED.

FIG. 2 is a block diagram illustrating one representative electronics control architecture and associated components suitable for use in the base defibrillator unit 110. In the illustrated embodiment, the electronic components include a defibrillator controller 130, memory 133, a wireless communications module in the form of Bluetooth module 134, a charging power regulator 140, a voltage booster 145 (which may have multiple stages), a high voltage capacitor 150 for temporarily storing sufficient electrical energy suitable to provide a defibrillation shock, shock discharge control circuitry 160, internal discharge circuitry 168, pad related sensing circuitry 162 and relays 169, power storage unit 170, battery regulator 193, status indicator(s) 175, speaker(s) 180 and one or more electrical connectors (e.g., interface connector 190, mobile connector port 195, charger connector (not shown), etc). The charging power regulator 140 and voltage booster 145 which cooperate to control the charging of the shock discharge capacitor 150 are sometimes referred to herein as a charging circuit. In some embodiments the base defibrillator unit may also include components such as low voltage step-up circuit 161, ESD protection circuit 167, power-on button 183 and other buttons 186.

The defibrillator controller 130 is configured to control the operation of the base defibrillator unit and to direct communications with external devices, as appropriate. In some embodiments, the defibrillator controller includes one or more processors arranged to execute software or firmware having programmed instructions for controlling the operation of the base unit, directing interactions with a user and communications with external components.

The Bluetooth module 134 supports BLE communications and broadcasts status message advertisements as described above at the direction of Defibrillator controller 130.

The base defibrillator unit 110 may optionally be configured so that it is capable of drawing power from certain other available power sources beyond power storage unit 170 to expedite the charging of shock discharge capacitor 150. The charging power regulator 140 is configured to manage the current draws that supply the voltage booster, regardless of where that power may originate from. For example, in some embodiments, supplemental power may be supplied from a mobile device coupled to mobile connector port 195 or from a portable charger/supplemental battery pack coupled to charger connector 197.

The voltage booster 145 is arranged to boost the voltage from the operational voltage of power storage unit 170 to the desired operational voltage of the discharge capacitor 150, which in the described embodiment may be on the order of approximately 1400V-2000V (although the defibrillator may be designed to attain any desired voltage). In some embodiments, the boost is accomplished in a single stage, whereas in other embodiments, a multi stage boost converter is used. A few representative boost converters are described in the incorporated U.S. Pat. No. 10,029,109. By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 151 is provided to read the voltage of the capacitor 150. The voltage sensor 151 may take the form of a voltage divider or any other suitable form. This capacitor voltage reading is utilized to determine when the shock discharge capacitor 150 is charged suitably for use. The sensed voltage is provided to controller 130 which determines when the capacitor 150 is charged sufficiently to deliver a defibrillation shock. The capacitor 150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively higher energy impulses in subsequently administered shocks (up to a point).

The discharge circuitry 160 may take a wide variety of different forms. In some embodiments, the discharge circuitry 160 includes an H-bridge along with the drivers that drive the H-bridge switches. The drivers are directed by defibrillator controller 130. The H-bridge outputs a biphasic (or other multi-phasic) shock to patient electrode pads 116 through relays 169. The relays 169 are configured to switch between an ECG detection mode in which the patient electrode pads 116 are coupled to the pad related sensing circuitry 162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 162 may include a variety of different functions. By way of example, this may optionally include a pad connection sensor 164, ECG sensing/filtering circuitry 165 and impedance measurement filter 166. The pad connection sensor is arranged to detect the pads are actually connected to (plugged into) the base defibrillator unit 110. The ECG sensing/filtering circuitry 165 senses electrical activity of the patient's heart when the pads are attached to a patient. The filtered signal is then passed to defibrillator controller 130 for analysis to determine whether the detected cardiac rhythm indicates a condition that is a candidate to be treated by the administration of an electrical shock (i.e., whether the rhythm is a shockable rhythm) and the nature of the recommended shock. When a shockable rhythm is detected, the controller 130 directs the user appropriately and controls the shock delivery by directing the H-bridge drivers appropriately.

In some embodiments, the power storage unit 170 takes the form of one or more batteries such as rechargeable Lithium based batteries including Lithium-ion and other Lithium based chemistries, although other power storage devices such as one or more supercapacitors, ultracapacitors, etc. and/or other battery chemistries and/or combinations thereof may be used as deemed appropriate for any particular application. The power storage unit 170 is preferably rechargeable and may be recharged via any of a variety of charging mechanism. In some embodiments, the power storage unit 170 takes the form of a rechargeable battery. For convenience and simplicity, in much of the description below, we refer to the power storage unit 170 as a rechargeable battery. However, it should be appreciated that other types of power storage devices can readily be substituted for the battery. Also, the singular term "battery" is often used and it should be appreciated that the battery may be a unit composed of a single battery or a plurality of individual batteries and/or may comprise one or more other power storage components and/or combinations of different power storage units.

In some embodiments, the base defibrillator unit 110 is capable of drawing power from other available power sources for the purpose of one or both of (a) expediting the charging of shock discharge capacitor 150 and (b) recharging the power storage unit 170. In some embodiments, the battery can be recharged using one or more of the externally accessible connector port 195, a dedicated charging station, a supplemental battery pack (portable charger), an interface unit 200, etc. as will be described in more detail below. When wireless charging is supported, the base defibrillator unit may include a wireless charging module 174 configured to facilitate inductive charging of the power storage unit 170 (e.g. using an inductive charging station 294, or other devices that support inductive charging, as for example an inductively charging battery pack, a cell phone with inductive charging capabilities, etc.).

The base unit also includes a number of software or firmware control algorithms installed in memory 133 and executable on the defibrillator controller 130. The control algorithms have programmed instructions suitable for controlling operation of the base unit and for coordinating the described broadcasts, as well as any point-to-point communications between the base unit 110 and the interface unit 200, connected devices 105, and/or any other attached or connected (wirelessly or wired) devices. These control routines include (but are not limited to): communication control algorithms, heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices (e.g. interface unit 200, mobile communication device 105) during an emergency; battery charge control algorithms for managing the charging of power storage unit 170; testing and reporting algorithms for managing and reporting self-testing of the base unit; software update control algorithms and verification files that facilitate software updates and the verification of the same.

In some embodiments, a single processor is used as defibrillator controller 130. In other embodiments, multiple processors may be used. For example, the defibrillator controller 130 may include a master processor and a slave processor, with the slave processor being solely responsible for managing the charging and discharging of the discharge capacitor 150.

Figure 3:
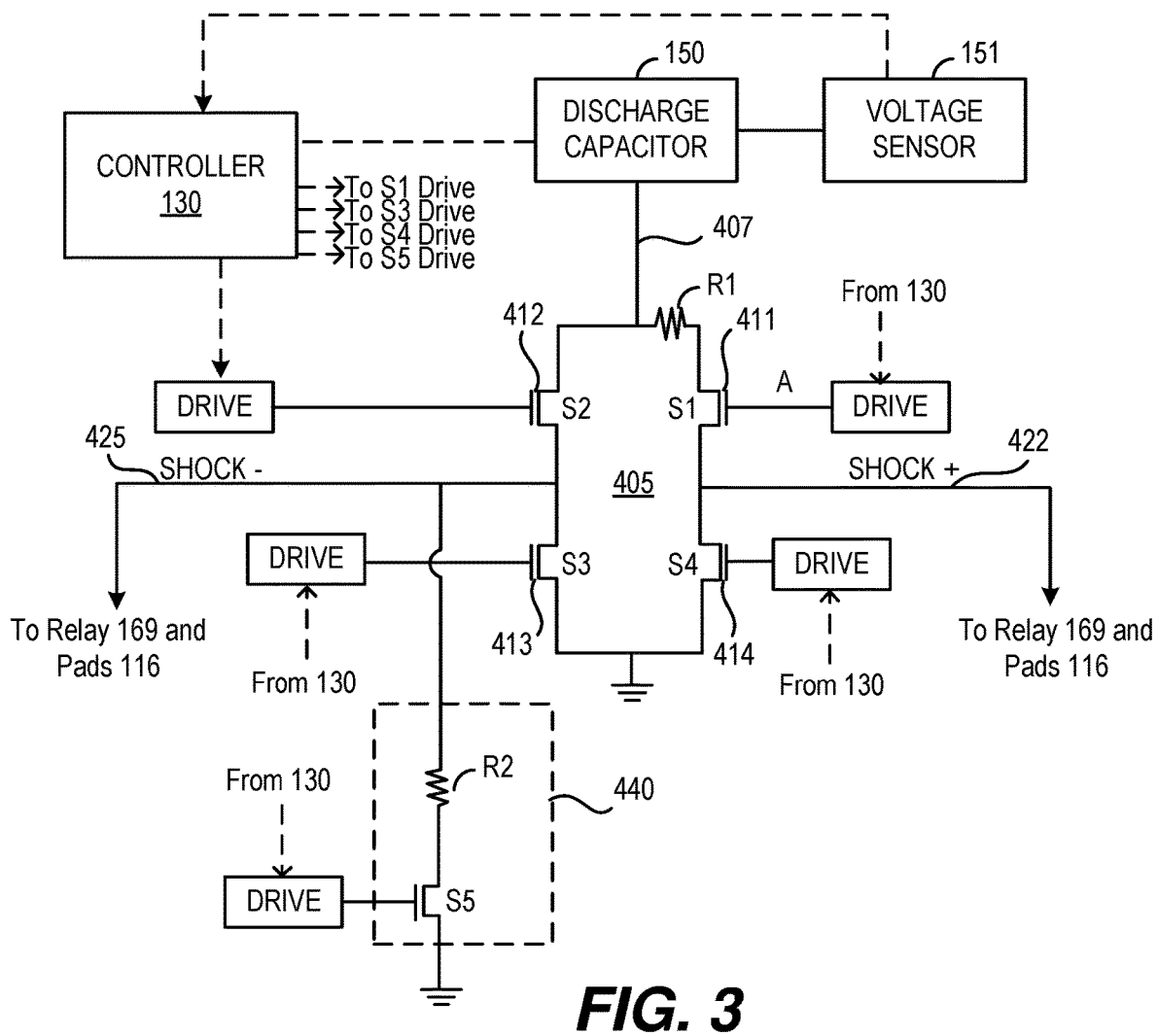
FIG. 3 is a circuit diagram illustrating a discharge test circuit in accordance with one embodiment.

FIG. 3 shows a representative discharge circuit in accordance with a particular embodiment. In the illustrated embodiment, the core of the discharge circuit 160 takes the form of an H-Bridge 405. H-bridges are commonly used in defibrillators to deliver bi-phasic (or other multi-phasic) defibrillation shocks. Since H-bridge based defibrillator discharge circuits are well known, the control and operation of the H-bridge during discharge is not described in detail herein. The most common defibrillation shock waveforms are truncated exponential bi-phasic waveforms. However, as is well known in the art, the H-bridge can be controlled in different manners to provide a variety of different resultant waveforms including multi-phasic waveforms having more than two phases, and various waveforms that have more rectangular, sawtooth or other desired shaped pulse phases.

In some implementations, the H-bridge is packaged as an integrated circuit power device that is capable of handling the voltages and currents that are used in defibrillation. Of course, in other embodiments the H-Bridge may be formed from discrete components, other integrated circuit power devices and/or any other suitable combination of components.

The input 407 to H-bridge 405 is connected to shock discharge capacitor 150 (sometimes referred to as shock delivery capacitor). The H-bridge includes four switches S1, S2, S3 and S4, the gates of which are exposed as pins 411, 412, 413 and 414 in the illustrated embodiment. The H-bridge 405 has two outputs that are referred to herein as the shock+ output 422 and shock-output 425. Each of the outputs is electrically connected to an associated electrode pad 116—typically through an associated one of the relays 169. In practice, each output line 422, 425 often has its own relay element so that a pair of relay elements are used—one for each output line. The relay elements may be packaged separately or together (e.g., a double pole, double throw relay) Each switch has associated driver circuitry (not shown) suitable to activating and deactivating the switch. Since such driver circuitry is conventional it is not explained in detail herein.

In the illustrated embodiment, a resistive component R1, which may take the form of a relatively low resistance resistor is provided in the path associated with switch S1 such that any current passing through S1 also passes through the resistive component R1 but current passing through S2 does not pass through the resistor R1. In FIG. 3, resistor R1 is shown on the upstream side of switch S1 which is preferred, although it should be appreciated that in other embodiments resistor R1 may be located downstream of switch S1 so long as it does not impact current flowing through branches of the H-bridge not involving S1. One function of the resistor R1 may be to help shape or at least scale the first phase of a shock waveform, without impacting the second phase of a shock waveform. This can be particularly useful to help control the peak current in the first phase of the shock waveform when the capacitor might otherwise discharge quicker than desired, as may be the case with low impedance patients. The actual resistance of resistive component R1 may vary to meet the needs of any particular design—but in some embodiments, resistances in the range of 1-10 ohms are appropriate.

In the illustrated embodiment, resistive component R1 takes the form of a resistor. However, in other embodiments, other components having an appropriate resistance such as a power inductors or combinations of components may be used (e.g., a resistor and an inductor).

In some alternative embodiments the resistive component R1 may be positioned between the capacitor 150 and the H-bridge 405 so that it affects both S1 and S2 although this is often less desirable because it may impact current flowing through switch S2 more than desired. When more control of the second phase of the shock waveform is desired a separate resistive component (not shown) may be provided in the flow path associated with switch S2. Generally, it is preferable that the resistance in the path associated with the first phase of the defibrillation shock (e.g. the path associated with S1 in the example) be higher than the resistance in the path associated with the second phase of the defibrillation shock (e.g., the path associated with S2 in the example).

FIG. 3 also shows a test circuit 440 that includes a switch S5 and a resistive component R2 which also may also take the form of a resistor. The test circuit 440 also serves as internal discharge circuit 168. Resistor R2 is connected to shock-output 425 but is not in the electrical path to relay 169 and pads 116 so that current passing through the relay 169 and pads 116 does not pass through Resistor R2. Switch S5 is coupled to resistor R2 downstream of the resistor. As will be described in more detail below, test circuit 440 is used in the testing of the discharge circuit H-bridge and may also be used to internally dissipate charge from shock delivery capacitor 150 if and when desired.

Defibrillation controller 130 controls the activation and deactivation of the various H-bridge switches S1-S4, test circuit switch S5 and relay 169 through appropriate driver circuits (not separately shown). The controller 130 also controls the charging of the discharge capacitor 150.

To use the AED, the electrode pads are placed on the patient and the capacitor 150 is charged to a level suitable for defibrillation (which typically is to a voltage in the range of 1400 to 2000 volts for an AED that uses a biphasic waveform, although the actual charge voltage may vary in accordance with the constraints of any particular design). To deliver a biphasic shock, relay 169 is switched to the discharge circuit 160 and switches S1 and S4 are opened to initiate delivery of the first phase of the defibrillation shock. During the first defibrillation shock phase, switches S2 and S3 remain closed. When the first shock phase is completed, at least S1 is typically turned off to terminate the first shock phase. After a brief inter-phase, the second phase of the defibrillation shock is delivered with switches S2 and S3 activated and switches S1 and S4 closed. The second phase of the shock may be terminated by turning off at least switch S2. The second shock phase has the opposite polarity as the first phase and thus by convention, the first phase is often referred to as the positive phase and the second phase is often referred to as the negative phases. If additional phases are desired, the H-bridge can be controlled appropriately to deliver additional shock phases.

Figure 4:
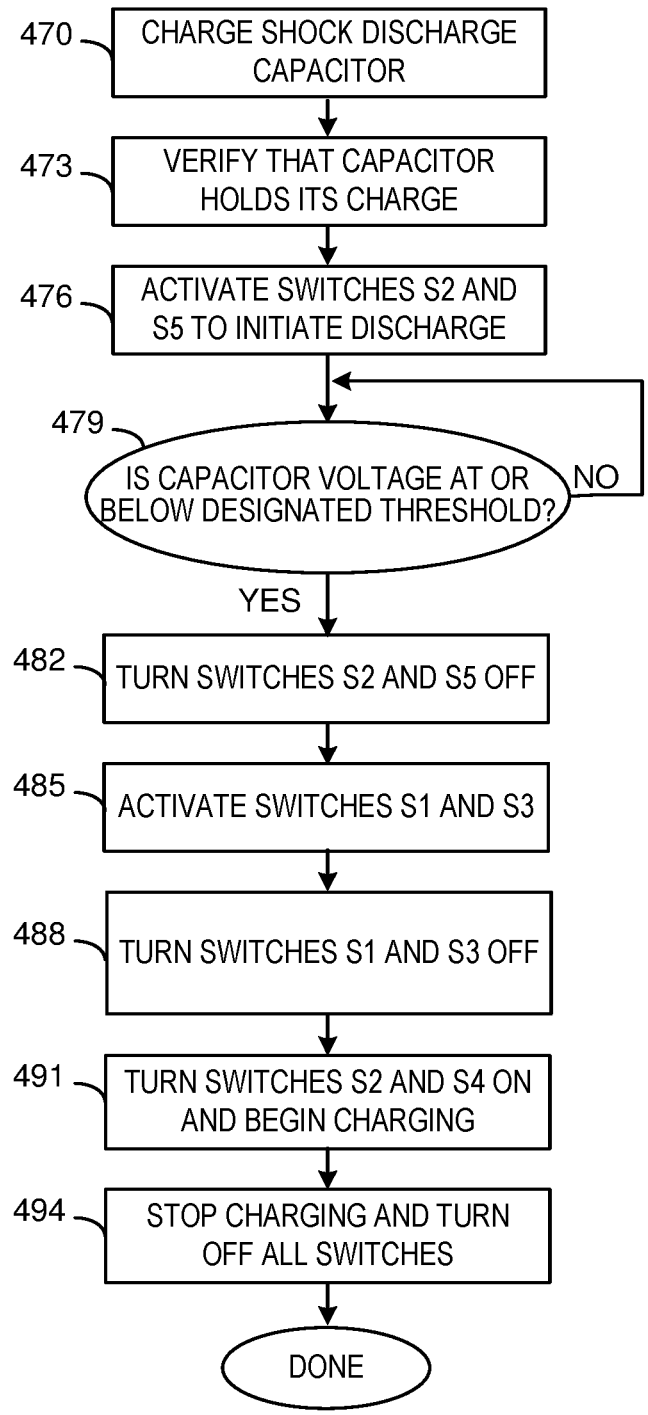
FIG. 4 is a flow chart illustrating a method of testing a defibrillator discharge circuit in accordance with another embodiment.

Referring next to FIG. 4 in conjunction with FIG. 3 a method of testing the discharge circuit will be described. Initially the shock discharge capacitor 150 is charged as represented by box 470. The capacitor may be charged to any level deemed appropriate for testing. In some embodiments, the capacitor may be charged to the defibrillator's highest rated voltage. In AEDs that utilize a biphasic waveform, shocks are typically delivered at voltages on the order of 1400 to 2000 volts. Thus, in some implementations charging the capacitor to a voltage in that range (e.g., 1400-2000 volts) may be appropriate. However, it should be appreciated that the capacitor can be charged to any level that is deemed appropriate for testing. For the purposes of this explanation, it will be assumed that the capacitor is charged to 2000 volts.

Defibrillator controller 130 directs the charging of the shock discharge capacitor 150 when a test is desired. As discussed above, the voltage sensor 151 monitors the voltage of the capacitor as it is charged and so informs the defibrillator controller. When the voltage of the capacitor reaches the desired level (e.g., 2000 volts), controller 130 terminates the charging.

It should be appreciated that charging the shock discharge capacitor 150 to 2000 volts implicitly tests the dielectric strength of switches S1 and S2 since the switches are exposed to the voltage of the capacitor and would fail if they cannot withstand the capacitor voltage. Any such failure of switches S1 and S2 will be noticeable because the capacitor would not hold its charge. The controller 130 verifies that the capacitor is able to hold is charge as represented by block 473. The results of the verification are preferably logged and if the tests failed in any way, the nature of the fault is recorded and any desired notifications may be generated and/or the defibrillator status may be updated as appropriate.

The capacitor charge holding test may be accomplished by continuing to monitor the voltage of the capacitor. If the capacitor is not able to hold a charge as expected (e.g., the voltage of the capacitor drops more than expected due to the small drain of the voltage sensor itself) the failure is recorded in the test log. When desired, the failure may additionally or alternatively be logged as a fault in an appropriate fault log. It should be appreciated that charging the capacitor also has the effect of testing the charging circuit to verify that the charging circuitry is working properly. Furthermore, the charge time is preferably monitored to verify that the charging circuitry can charge the discharge capacitor within the desired capacitor charging period. Again, the results of such capacitor charge timing testing can be logged appropriately.

After capacitor 150 has been charged, switch S5 is turned on, and thereafter switch S2 is turned on as represented by block 476. Activating switches S5 and S2 creates a discharge path from capacitor 150 to ground via switch S2, resistor R2 and switch S5. The rate at which the capacitor 150 discharges along this path is dictated in large part by the resistance of resistor R2. Thus, selection of the resistance of resistive element R2 effectively controls the capacitor discharge rate. The specific resistance of resistor R2 can vary widely based on the needs of any particular defibrillator design. By way of example, resistances in the range of 100 to 10,000 ohms work well in many implementations.

In the described approach, switch S5 is turned on before S2. This helps ensure that switch S5 is not exposed to the full capacitor potential (e.g. 2000 volts) which could occur if switches S2 and S5 were activated in the opposite order. Rather, during testing, S5 is exposed to relatively minimal voltages since is positioned downstream of resistor R2. It should be appreciated that if switch S2 is activated before switch S5, switch S5 could potentially be exposed to the full capacitor voltage (e.g., 2000 volts).

Since S5 is indirectly coupled to shock-output 425, the highest voltages that S5 would potentially be exposed to over the life of the defibrillator is the peak voltage of the second phase of an actual defibrillation shock. This might be a voltage on the order of 1000 volts or 1200 volts max. As will be appreciated by those familiar with the art, switches (e.g. IGBTs) that are rated to 2000 volts are much more expensive and much larger than switches that are rated to 1000 volts or 1200 volts. Therefore, controlling the order in which switches S5 and S2 are activated during a test discharge allows the use of more cost and space effective components in the test circuit.

This draining of the capacitor 150 through switch S2, resistor R2 and switch S5 inherently tests the switching ability of switch S2. As the capacitor 150 is drained, the controller 130 continues to monitor the capacitor's voltage as represented by decision block 479. When the capacitor reaches a designated threshold voltage, switches S2 and S5 are turned off as represented by block 482. Preferably switch S2 is turned off before switch S5. An advantage of turning off switch S2 first is that it provides a mechanism for verifying that the voltage sensor circuit and the capacitor discharge control circuitry are working properly. This can be particularly useful in implementations that control the duration of the defibrillation shock phases based at least in part on the capacitor voltage level rather than simply discharge times. This requires the ability to turn off selected H-bridge switches at precise voltages during defibrillation shock discharges. The same capacitor charge monitoring hardware/algorithms and discharge circuitry control are preferably used to determine when to turn off switch S2. By checking the capacitor voltage after switch S2 is turned off, the processor can verify that the voltage sensing circuit and voltage monitoring function of the defibrillator controller are working properly. E.g., that the voltage monitor and the capacitor discharge control algorithm and circuitry were able to monitor and control the discharge of the capacitor within an appropriate tolerance as required. Again, the results of this check may be logged in the test log and any failures may be recorded appropriately.

The threshold voltage at which the capacitor draining is turned off may vary in accordance with the needs of any particular system. By way of example, voltages on the order of 100V are suitable for some implementations as will be described in more detail below. In other embodiments, higher or lower trigger voltages may used.

Additionally, the time that is taken to drain the capacitor to the desired voltage level threshold (trigger) voltage through switch S2, resistor R2 and switch S5 is preferably measured and logged. This drain time measurement is used to verify that the equivalent resistance/inductance (equivalent circuit characteristics) of the circuit is still as expected. If the drain time is significantly longer or shorter than expected, it may be assumed that something is wrong with some aspect of the discharge and/or disarm circuits and an appropriate fault is generated.

After switches S2 and S5 have been turned off, the next phase of the discharge test is initiated by activating switches S1 and S3 as represented by block 485. This creates a path from the discharge capacitor 150 to ground through resistor R1 which provides the only substantial resistance in the illustrated embodiment. Thus, when switches S1 and S3 are turned on, the current through those switches is a function of the capacitor voltage and the resistance of resistive element R1. In some implementations the capacitor's starting voltage level (the voltage level at which the previous discharge phase was turned off) is chosen so that a maximum current in the range of 20-50 amps flows through the active switches (S1 and S3) and the associated legs of the H-bridge 410. This serves to test the current carrying capacity of the active switches, including switch S1. In practice, 20-50 amps is on the scale of or higher than the current that will be delivered in a defibrillation shock delivered to most patients during emergency use of the defibrillator. Thus, this phase of the discharge test serves to verify that switch S1 is capable of handling the current associated with delivering a defibrillation shock. Again, the results of this phase of the discharge test may be logged appropriately.

In some embodiments, the second test discharge phase is terminated (i.e., switches S1 and S3 are turned off) when the capacitor reaches a designated threshold voltage. This serves as another mechanism for testing both the voltage monitor and the capacitor discharge control algorithms and circuitry. In other embodiments, the capacitor may be fully drained before turning of switches S1 and S3. When switches S1 and S3 are turned off, the second test phase is completed as represented by block 488.

The drain time through switches S1 and S3 is also measured (and logged) to verify that the equivalent resistance/inductance (equivalent circuit characteristics) of the circuit is still as expected. As discussed above, if the drain time is significantly longer or shorter than expected, it may be assumed that something is wrong with some aspect of the discharge circuit and an appropriate fault is generated.

It should be appreciated that the test current that is generated can be set to virtually any desired level by setting the capacitor voltage threshold at which switched S2 is turned off, taking into account the resistance of resistor R1.

Typically S3 would be turned on before S1 is turned on, although this is not a requirement since S3 is quite capable of handling voltages of 100 volts as might be presented if the switches are turned on in the opposite order.

After the second test discharge has been completed switches S2 and S4 are turned back on and the defibrillator controller 130 restarts charging of the capacitor 150 as represented by block 491. This begins a third test phase. With switches S2 and S4 active, the capacitor 150 is effectively shorted to ground and therefore it should not actually charge. This confirms that the switches activated in the third phase (switches S2 and S4) are working properly (e.g., that they can be turned on as desired). Any unexpected raise in the voltage of the capacitor 150 (as detected by voltage sensor 151) indicates a fault that may be logged appropriately. It should be appreciated that the charging in this portion of the discharge test does not need to last long since the voltage sensor 151 would very quickly see an increase in the capacitor voltage if the H-bridge is not conducting current as expected.

It is noted that the gate drive functionality of switched S1, S2, S3 and S5 were effectively tested in the previous tests and the shorted charging test (with switches S2 and S4 active) effectively tests the gate drive functionality of switch S4. The shorted charging test also effectively tests the current carrying capability of S4 at least to the level of the charging current.

Once the discharge has been verified, defibrillator controller 130 directs the charging circuit to stop charging and switches S2 and S4 are turned off so that all switches S1-S5 are turned off as represented by block 494 and the corresponding test results are logged. In the illustrated embodiment, the shorted charging test 491, 494 occurs after the other discharge tests. However, it should be apparent that the shorted testing test can readily be performed prior to the initial charging of the discharge capacitor 150 (step 470) or at other suitable times. Once all of the described tests have been performed, the discharge test is completed.

In still other embodiments, the second discharge test may be stopped with a relatively low voltage (e.g., at a voltage in the range of 10-40 volts—as for example, 20 volts). With switches S1 and S3 turned off and the relatively low voltage remaining on the capacitor, switches S2 and S4 may be turned on. As previously mentioned, this effectively shorts capacitor 150 to ground. As such, the capacitor should fully discharge. This is an alternate approach for confirming that the switches activated in the third test phase are working properly.

Although only a few embodiments of the invention have been described in detail, it should be appreciated that the invention may be implemented in many other forms without departing from the spirit or scope of the invention. In the primary described embodiment, the discharged testing is directed by the defibrillator controller 130 which may execute a test discharge control algorithm stored in the controller's memory 133. This control includes directing the charging of the capacitor 150, monitoring voltage sensor 151 and directing the switching of the various switches S1-S5.

Since test circuit 440 can be used to discharge the capacitor, it can also be used in circumstances other than testing in which it may be desirable to reduce the voltage of the capacitor or totally drain the capacitor. That is, switches S2 and S5 may be turned on to drain or partially drain capacitor 150 at any time. For example, if there is a desire to reduce the charge on the capacitor prior to delivering a defibrillation shock for any reason, that may be accomplished using switches S2 and S5. As always, the voltage sensor 151 monitors the capacitor charge level during any such draining and defibrillator controller 130 may stop the draining at any desired voltage by turning off switch S2. The ability to reduce the capacitor voltage can be useful in a variety of situations including: (a) if/when a user switches from and adult to pediatric operational mode after the capacitor has been charged; (b) if/when there is a decision not to deliver a shock after the capacitor has been charged; (c) to drain residual capacitor charges after the defibrillator has been used; etc.

Therefore, the present embodiments should be considered illustrative and not restrictive and the invention is not to be limited to the details given herein, but may be modified within the scope and equivalents of the appended claims.

What is claimed is:

1. A defibrillator comprising:
a shock discharge capacitor capable of temporarily storing and discharging sufficient energy to deliver a defibrillation shock to a patient;
an H-bridge having first, second, third and fourth switches, an input electrically coupled to the shock discharge capacitor, a first output configured to be electrically coupled to a first defibrillation electrode pad and a second output configured to be electrically coupled to a second defibrillation electrode pad;
a test discharge circuit including a test resistive element and a fifth switch, the test resistive element being electrically coupled between the fifth switch and the second output so that current passing between the second output and the second defibrillation electrode does not pass through the test resistive element, and so that electrical current passing through the fifth switch from the second output passes through the test resistive element; and
a controller configured to direct operation of the switches of the H-bridge in an operational mode to deliver a defibrillation shock, and to direct operation of the switches of the H-bridge and the test discharge circuit in a test mode to facilitate at least partially discharging the shock discharge capacitor internally within the defibrillator through the fifth switch and the resistive element; and
wherein in the test circuit is electrically coupled to the H-bridge so that the controller may direct at least a partial internal discharge of the shock discharge capacitor that passes through the test circuit and a single leg of the H-bridge.

2. A defibrillator as recited in claim 1 wherein the controller is further configured to direct operation of the switches of the H-bridge and the test discharge circuit in a test mode to facilitate testing each of the H-bridge switches.

3. A defibrillator as recited in claim 1 further comprising a first resistive element in a first electrical path between the shock discharge capacitor and the first H-bridge output that includes the first H-bridge switch, wherein the first resistive element is positioned so that:
current passing through the first H-bridge switch also passes through the first resistive element;
current passing from the shock discharge capacitor through the second H-bridge switch does not pass through the first resistive element; and
no additional switches are required to prevent current passing through the second H-bridge switch from passing through the first resistive element.

4. A defibrillator as recited in claim 1 wherein the resistance of the test resistive element is in the range of 100 to 10,000 ohms.

5. A defibrillator as recited in claim 1 further comprising:
the first and second defibrillation electrode pads; and
first and second relay elements, the first relay element being positioned in an electrical path between the first output and the first defibrillation electrode pad and the second relay element being positioned in an electrical path between the second output and the first defibrillation electrode pad.

6. A defibrillator as recited in claim 5 further comprising a double pole double throw relay that includes the first and second relay elements.

7. A defibrillator as recited in claim 1 wherein the at least partial internal discharge occurs through a path consisting essentially of the second switch, the test resistive element and the fifth switch.

8. A defibrillator comprising:
a shock discharge capacitor capable of temporarily storing and discharging sufficient energy to deliver a defibrillation shock to a patient;
an H-bridge having first, second, third and fourth switches, an input electrically coupled to the shock discharge capacitor, a first output configured to be electrically coupled to a first defibrillation electrode pad and a second output configured to be electrically coupled to a second defibrillation electrode pad;
a test discharge circuit including a test resistive element and a fifth switch, the test resistive element being electrically coupled between the fifth switch and the second output so that current passing between the second output and the second defibrillation electrode does not pass through the test resistive element, and so that electrical current passing between the second output and the fifth switch passes through the test resistive element;
a controller configured to direct operation of the switches of the H-bridge in an operational mode to deliver a defibrillation shock, and to direct operation of the switches of the H-bridge and the test discharge circuit in a test mode to facilitate at least partially discharging the shock discharge capacitor through the fifth switch; and
a first resistive element in a first electrical path between the shock discharge capacitor and the first H-bridge output that includes the first H-bridge switch, wherein the first resistive element is positioned so that current passing through the first H-bridge switch also passes through the first resistive element, and current passing through the second H-bridge switch does not pass through the first resistive element, and no additional switches are required to prevent current passing through the second H-bridge switch from passing through the first resistive element.

9. A defibrillator as recited in claim 8 wherein the resistance of the first resistive element is in the range of 1 to 10 ohms.

10. A defibrillator comprising:
a shock discharge capacitor capable of temporarily storing and discharging sufficient energy to deliver a defibrillation shock to a patient;
an H-bridge having first, second, third and fourth switches, an input electrically coupled to the shock discharge capacitor, a first output configured to be electrically coupled to a first defibrillation electrode pad and a second output configured to be electrically coupled to a second defibrillation electrode pad;
a test discharge circuit including a test resistive element and a fifth switch, the test resistive element being electrically coupled between the fifth switch and the second output so that current passing between the second output and the second defibrillation electrode does not pass through the test resistive element, and so that electrical current passing between the second output and the fifth switch passes through the test resistive element; and
a controller configured to direct operation of the switches of the H-bridge in an operational mode to deliver a defibrillation shock, and to direct operation of the switches of the H-bridge and the test discharge circuit in a test mode to facilitate at least partially discharging the shock discharge capacitor through the fifth switch, and to cause a charging circuit to attempt to charge the shock discharge capacitor during a test phase with the second and fourth switches on and the first, third and fifth switches off.

11. A defibrillator comprising:
a shock discharge capacitor capable of temporarily storing and discharging sufficient energy to deliver a defibrillation shock to a patient;
an H-bridge having first, second, third and fourth switches, an input electrically coupled to the shock discharge capacitor, a first output configured to be electrically coupled to a first defibrillation electrode pad and a second output configured to be electrically coupled to a second defibrillation electrode pad;
a test discharge circuit including a test resistive element and a fifth switch, the test resistive element being electrically coupled between the fifth switch and the second output so that current passing between the second output and the second defibrillation electrode does not pass through the test resistive element, and so that electrical current passing between the second output and the fifth switch passes through the test resistive element; and
a controller configured to direct operation of the switches of the H-bridge in an operational mode to deliver a defibrillation shock, and to direct operation of the switches of the H-bridge and the test discharge circuit in a test mode to facilitate at least partially discharging the shock discharge capacitor through the fifth switch, wherein the controller is configured to direct a test discharge by:
causing the second and fifth switches to be on with the first, third and fourth switches off for a first test phase to cause the shock discharge capacitor to at least partially discharge through the test resistive element;
causing the second and fifth switches to be turned off when the shock discharge capacitor drains to a designated voltage; and
causing the first and third switches to be on for a second test phase with the second, fourth and fifth switches off after the shock discharge capacitor has drained to the designated voltage.

12. A defibrillator as recited in claim 11 wherein the controller is further configured to cause a charging circuit to attempt to charge the shock discharge capacitor for a third test phase with the second and fourth switches on and the first, third and fifth switches off.

13. A method of testing a defibrillator discharge circuit that includes an H-bridge having first, second, third and fourth switches, an input electrically coupled to a shock discharge capacitor, a first output configured to be electrically coupled to a first defibrillation electrode pad, a second output configured to be electrically coupled to a second defibrillation electrode pad, and a first resistor in a first electrical path between the shock discharge capacitor and the first H-bridge output, the defibrillator discharge circuit being tested using a discharge test circuit that includes a fifth switch and a test resistor, the method comprising:
causing the second and fifth switches to be on with the first, third and fourth switches off to cause the shock discharge capacitor to at least partially discharge through the second switch, the test resistor and the fifth switch during a first test phase;
turning the second and fifth switches off after the shock discharge capacitor reaches a designated voltage; and
causing the first and third switches to be on for a second test phase with the second, fourth and fifth switches off after the shock discharge capacitor has reached the designated voltage to further discharge the shock discharge capacitor through the first resistor and the first and third switches.

14. A method as recited in claim 13 further comprising initiating charging the shock discharge capacitor for a third test phase with the second and fourth switches on and the first, third and fifth switches off.

15. A method of testing a defibrillator discharge circuit that includes an H-bridge having first, second, third and fourth switches, the method comprising:
charging a shock discharge capacitor to a first designated voltage level suitable for delivering a defibrillation shock;
dissipating the charge on the shock discharge capacitor to a second designated voltage level through the second switch in a first test discharge phase, wherein the charging of the shock discharge capacitor and the first test discharge phase together expose the first, second, and third switches of the H-bridge to the designated voltage to test a dielectric strength of each of the first, second and third switches of the H-bridge; and dissipating the charge on the shock discharge capacitor from the second designated voltage level through the first switch in a second test discharge phase.

16. A method as recited in claim 15 wherein a peak current in the second test discharge phase exceeds 20 amps.

17. A method as recited in claim 15 wherein during the second test discharge phase, dissipating current flows through both the first switch and the third switch.

18. A method as recited in claim 15 further comprising initiating charging the shock discharge capacitor for a third test phase with the second and fourth switches on and the first, third and fifth switches off.

19. A method of reducing a charge on a defibrillator shock discharge capacitor in a defibrillator including the shock discharge capacitor and a discharge circuit that includes an H-bridge having first, second, third and fourth switches, an input electrically coupled to the shock discharge capacitor, a first output configured to be electrically coupled to a first defibrillation electrode pad and a second output configured to be electrically coupled to a second defibrillation electrode pad, the method comprising:
- turning a fifth switch on that is electrically connected to an effective ground and electrically connected to the second output via a resistive element; and
- turning the second switch on after the fifth switch has been turned on with the first, third and fourth switches off to cause the shock discharge capacitor to at least partially discharge through a discharge path that includes the second switch, the resistive element and the fifth switch.

20. A method as recited in claim 19 wherein the discharge path consists essentially of the second switch, the resistive element and the fifth switch.

21. A defibrillator comprising:
- a shock discharge capacitor capable of temporarily storing and discharging sufficient energy to deliver a defibrillation shock to the patient;
- an H-bridge having first, second, third and fourth switches, an input electrically coupled to the shock delivery capacitor, a first output configured to be electrically coupled to a first defibrillation electrode pad and a second output configured to be electrically coupled to a second defibrillation electrode pad;
- a first resistive element in a first electrical path between the shock discharge capacitor and the first H-bridge output that includes the first H-bridge switch, wherein current passing from the shock discharge capacitor to the first output through the first H-bridge switch also passes through the first resistive element and wherein current passing from the shock discharge capacitor to the second output through the second H-bridge switch does not pass through the first resistive element, and wherein the resistance of the first resistive element is greater than a total resistance between the shock discharge capacitor and the second H-bridge switch; and
- a defibrillator controller configured to direct operation of the switches of the H-bridge in an operational mode to deliver a biphasic or multi-phasic defibrillation shock, wherein an initial phase of current for the defibrillation shock passes through the first H-bridge switch and the first resistive element and not the second H-bridge switch and a second phase of the defibrillation shock that follows the initial phase passes through the second H-bridge switch and not the first H-bridge switch and the first resistive element.

22. A defibrillator as recited in claim 21 wherein no resistive elements are provided in a conductive path between the shock discharge capacitor and the second H-bridge switch.

23. A defibrillator comprising:
- a shock discharge capacitor capable of temporarily storing and discharging sufficient energy to deliver a defibrillation shock to the patient;
- an H-bridge having first, second, third and fourth switches, an input electrically coupled to the shock delivery capacitor, a first output configured to be electrically coupled to a first defibrillation electrode pad and a second output configured to be electrically coupled to a second defibrillation electrode pad;
- an H-bridge test circuit including a fifth switch electrically coupled between the H-bridge and an effective ground; and
- a controller configured to direct operation of the switches of the H-bridge in an operational mode to deliver a defibrillation shock via the first and second outputs, and to direct operation of the switches of the H-bridge and the fifth switch in a test mode to internally discharge the shock discharge capacitor in a plurality of phases that utilize different discharge paths, wherein each internal discharge phase causes current to pass through at least one of the H-bridge switches and at least one of the internal discharge phases causes current to pass through the fifth switch in addition at least one of the H-bridge switches; and
- wherein in the test mode, no switches other than one or more of the H-bridge switches and the fifth switch are activated during the multi-phase discharge test.

24. A defibrillator as recited in claim 23 wherein the defibrillator controller is configured to cause the shock discharge capacitor to be charged to an operating voltage suitable for delivering the defibrillation shock in the test mode.

* * * * *